US00PP35370P2

(12) United States Plant Patent
Bergman

(10) Patent No.: US PP35,370 P2
(45) Date of Patent: Sep. 5, 2023

(54) ***MANDEVILLA* PLANT NAMED 'MANZ0022'**

(50) Latin Name: ***Mandevilla sanderi* (Hemsl.) Woodson**
Varietal Denomination: MANZ0022

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/803,478

(22) Filed: Jul. 28, 2022

(51) Int. Cl.
*A01H 5/00* (2018.01)
*A01H 6/08* (2018.01)

(52) U.S. Cl.
USPC ..... Plt./232

(58) Field of Classification Search
USPC ..... Plt./227, 232
See application file for complete search history.

*Primary Examiner* — Karen M Redden
(74) *Attorney, Agent, or Firm* — Dale Skalla

(57) ABSTRACT

A new *Mandevilla* plant named 'MANZ0022' particularly distinguished by its strong pink slightly ruffled flower, fast flowering response, glossy and smooth dark green foliage, bushy plant habit with a tendency to produce vines under low light growing conditions and with excellent branching and flower production.

1 Drawing Sheet

Latin name of the genus and species of the plant claimed: *Mandevilla sanderi* (Hemsl.) Woodson.

Varietal denomination: 'MANZ0022'.

BACKGROUND OF THE NEW PLANT

The present invention comprises a new *Mandevilla*, botanically known as *Mandevilla sanderi*, and hereinafter referred to by the variety name 'MANZ0022'.

'MANZ0022' is a product of a planned breeding program. The new cultivar has dark pink flowers, slightly ruffled petal margins, glossy and smooth dark green foliage, compact and bushy plant habit and with excellent branching and flower production and fast flowering response.

'MANZ0022' originates from a hybridization made in a controlled breeding program in Amatitlan, Guatemala. The pollinations were made in 2012.

The female parent was an unpatented, proprietary plant identified as 'DIP-047', with pink flowers, small foliage size, and compact growth habit.

The male parent was an unpatented, proprietary plant identified as 'DIP-169', with strong pink flower color, compact growth habit, and fast flowering response.

The resulting seeds were sown in February 2014 and 'MANZ0022' was selected as one flowering plant within the progeny of the stated cross in December 2014 in a greenhouse in Gilroy, Calif.

The first act of asexual reproduction of 'MANZ0022' was accomplished when vegetative stem cuttings were propagated from the initial selection in February 2015 in a controlled environment in Gilroy, Calif.

BRIEF SUMMARY OF INVENTION

Horticultural examination of plants grown from cuttings of the plant initiated in June 2015 in Gilroy, Calif., and continuing thereafter, has demonstrated that the combination of characteristics as herein disclosed for 'MANZ0022' are firmly fixed and are retained through successive generations of asexual reproduction.

'MANZ0022' has not been observed under all possible environmental conditions. The phenotype may vary significantly with variations in environment such as temperature, light intensity and day length.

A Plant Breeder's Right for this cultivar has not yet been applied for. 'MANZ0022' has not been made publicly available prior to the effective filing date of this application, notwithstanding any disclosure that may have been made less than one year prior to the effective filing date of this application by the inventor or another who obtained 'MANZ0022' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

The accompanying photographic drawings show typical flower and foliage characteristics of 'MANZ0022' with colors being as true as possible with an illustration of this type.

Figure 1:
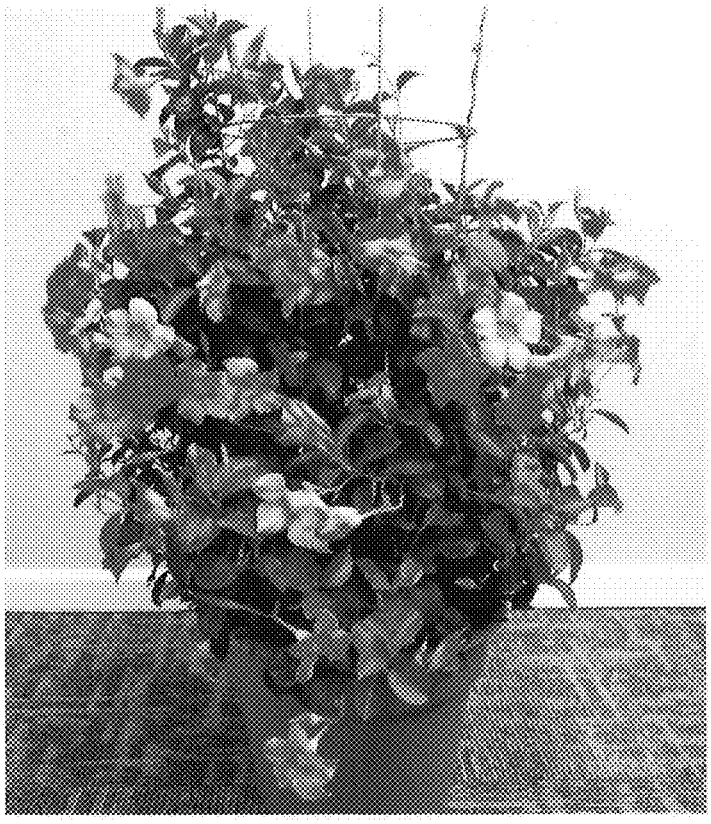
Figure 2:
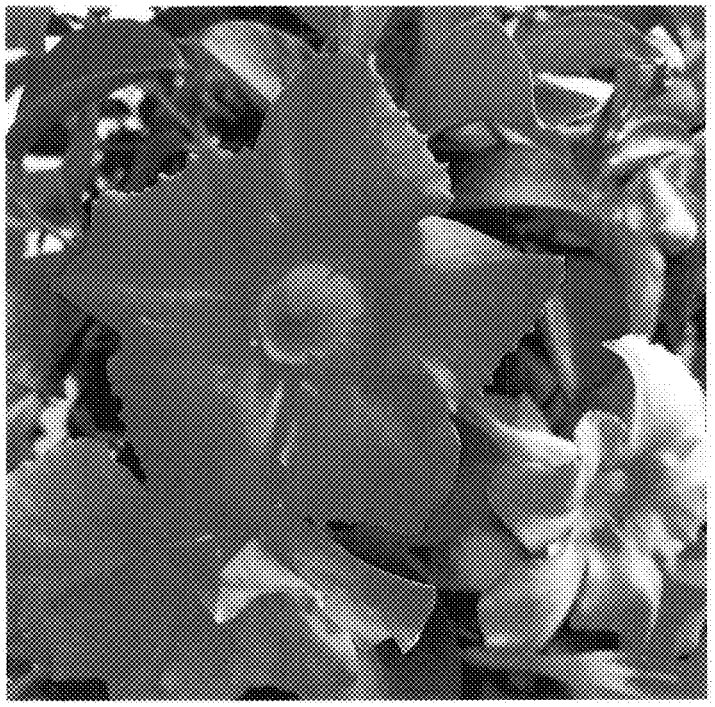

The photographic drawings show in FIG. 1, a flowering potted plant of the new variety and in FIG. 2, a close-up of the flowers.

DETAILED BOTANICAL DESCRIPTION

The aforementioned photographs were taken in June 2022 in Gilroy, Calif. The plants were growing in large pots outdoors. They were about 14 months in age.

TABLE 1

DIFFERENCES BETWEEN THE NEW VARIETY 'MANZ0022' AND A MOST SIMILAR VARIETY

| | 'MANZ0022' | 'Fisrix Pinka', U.S. Plant Pat. No. 20,644 |
|---|---|---|
| Plant habit: | More compact | Compact |
| Flower margin: | Slightly undulate | Smooth |
| Flowering response: | Faster | Slower |
| Flower color: | Less flower color fade | More flower color fade |

Plant:

*Form, growth, and habit.*—Perennial or sub-shrub, herbaceous younger stems, woody at base of older stems, semi-upright, with moderate tendency of developing vines depending on season and light intensity. Time for producing a commercial, flowering plant approximately is 20 weeks for one plant in a quart size container.

*Plant height.*—1 meter.

*Plant height (inflorescence included).*—1 meter.

*Plant width.*—76 cm.

Roots:

*Number of days to initiate roots.*—About 16-20 days at about 22 degrees C.

*Number of days to produce a rooted cutting plant.*—5 weeks at about 22 degrees C.

*Type.*—Fibrous, a little fleshy, free branching.

*Color.*—RHS 155D.

Foliage:

*Arrangement of leaves.*—Simple leaf, opposite and decussate.

*Immature leaf, color upper surface.*—RHS 137A.

*Immature leaf, color lower surface.*—RHS 184B anthocyanins present, mid-rib and veins RHS 138B.

*Mature leaf, color upper surface.*—RHS 139A.

*Mature leaf, color lower surface.*—RHS 138A.

*Length.*—5.4-6.5 cm.

*Width.*—3.8-4.2 cm.

*Shape.*—Ovate.

*Base shape.*—Mostly rounded, some attenuate.

*Apex shape.*—Mucronulate to cuspidate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 139B.

*Color of vein (midrib), lower surface.*—RHS 139D.

*Petiole color.*—RHS 142B.

*Length.*—0.9-1.3 cm.

*Diameter.*—0.2 cm.

*Petiole, texture.*—Glabrous.

Stem:

*Branching characteristics.*—Free branching.

*Quantity of main branches per plant.*—9-10.

*Color of stem.*—Oldest stems RHS 189A with RHS 199A overlay, younger stems RHS 139C.

*Length of stem.*—Widely ranging up to 1 meter.

*Diameter (at about mid-point).*—0.30 cm.

*Length of internodes.*—Widely ranging 1.0-17.0 cm.

*Stem, texture.*—Smooth and glabrous.

Inflorescence:

*Type of inflorescence.*—Raceme of several flowers, emerging from nodes of the stem.

*Number of flowers per inflorescence.*—1-3 open flowers per raceme.

*Blooming habit.*—Continuously through the summer months.

*Quantity of flowers per plant.*—About 50 in various stages of development.

*Lastingness of individual blooms on the plant.*—Approximately 8-10 days, depending on temperature.

*Fragrance.*—Absent.

Peduncle:

*Color.*—Green, RHS 141C.

*Length.*—2.0-3.0 cm.

*Diameter.*—0.25 cm.

*Texture.*—Smooth, glabrous, somewhat glossy.

Bud (just before opening/showing color):

*Color.*—Closest to RHS 61C.

*Length.*—7.7 cm.

*Width.*—1.8 cm.

*Shape.*—Elongated, spindle shape.

Immature flower:

*Diameter.*—6.2 cm.

*Vertical diameter.*—About 7.5 cm.

*Color upper surface.*—RHS 64C.

*Color lower surface.*—Closest to RHS 64D.

Mature flower:

*Shape.*—Funnelform, funnel shaped base, formed by 5 partly fused petals, with the petal lobes opening outwards, and slightly overlapping.

*Flower, horizontal diameter.*—8.0-8.5 cm.

*Flower, vertical diameter.*—About 6.8 cm.

*Flower, diameter of the funnel.*—1.7 cm.

*Flower color, general.*—Pink.

*Flower color, upper surface.*—Generally RHS 73A.

*Flower color, lower surface.*—RHS 63B.

*Color of the funnel, inner side.*—RHS 17A.

*Color of the funnel, outside.*—RHS 64C and RHS 64D.

*Petal, shape.*—Roughly ovate, asymmetric.

*Petal apex shape.*—Acute.

*Petal base shape.*—Fused.

*Petal margin.*—Mainly entire and mildly undulate.

*Petal length, from the corolla opening.*—3.8 cm.

*Petal width, maximum.*—3.6 cm.

*Corolla, texture of upper surface.*—Glabrous, papillose.

*Corolla, texture of lower surface.*—Glabrous, papillose.

*Pedicel, color.*—RHS 141C.

*Length.*—2.5-3.2 cm.

*Diameter.*—0.20 cm.

*Pedicel, texture.*—Smooth, glabrous.

Calyx:

*Form.*—5 sepals, closely attached to the base of the flower.

*Color, visible outer surface.*—RHS 145B.

*Length.*—1.0 cm.

*Width.*—0.40 cm.

*Shape.*—Subulate.

*Apex shape.*—Acute.

*Based.*—Fused.

*Margins.*—Entire.

*Texture, upper surface.*—Glabrous.

Reproductive organs:

Gynoecium:

*Pistil.*—1, with a 5-lobed stigma.

*Style length.*—2.0 cm.

*Diameter.*—0.05 cm.

*Style color.*—RHS 145D.
*Stigma color.*—RHS 145A.
*Stigma shape.*—Five lobed.
*Ovary color.*—RHS 144B.

Androecium:

*Stamens.*—5, surrounding the style and stigma.
*Filaments.*—Fused with the base of the flower.
*Anther.*—Elongated.
*Anther color.*—RHS 161D.
*Anther length.*—1.0 cm.
*Color of pollen.*—RHS 8D.
*Pollen amount.*—Moderate.

Fertility/seed set: Very low.

Disease/pest resistance: Has not been observed on this hybrid.

What is claimed is:

1. A new and distinct variety of *Mandevilla* plant named 'MANZ0022' substantially as illustrated and described herein.

* * * * *